(12) United States Patent
Falanga

(10) Patent No.: US 6,696,054 B1
(45) Date of Patent: Feb. 24, 2004

(54) METHOD AND APPARATUS FOR PRODUCING EFFERVESCENT SHAVING COMPOSITION

(76) Inventor: Paul M. Falanga, 5993 E. Chuckwalla Trail, Cave Creek, AZ (US) 85331

( * ) Notice: Subject to any disclaimer, the term of this patent is extended or adjusted under 35 U.S.C. 154(b) by 0 days.

(21) Appl. No.: 09/572,703

(22) Filed: May 16, 2000

(51) Int. Cl.⁷ .................................................. A61K 7/15
(52) U.S. Cl. ....................................................... 424/73
(58) Field of Search ................................... 424/73, 466

(56) References Cited

U.S. PATENT DOCUMENTS 5,948,439 A * 9/1999 Forman et al. ............. 424/466

* cited by examiner

*Primary Examiner*—James M. Spear
(74) *Attorney, Agent, or Firm*—Tod R. Nissle, P.C.

(57) ABSTRACT

A method for producing a shaving lather utilizes a composition produces a lather and carbon dioxide when a liquid is added to the shaving composition.

3 Claims, 3 Drawing Sheets

```
PROVIDE SOLID COMPOSITION INCLUDING SODIUM
BICARBONATE, AN ACID FORMING COMPOSITION AND AT
LEAST ONE SHAVING COMPONENT          10
                    │
                    ▼
ADD LIQUID TO SAID SOLID COMPOSITION TO CAUSE
THE SODIUM BICARBONATE TO REACT WITH THE ACID
FORMING COMPOSITION TO CHANGE THE pH OF THE
SOLID COMPOSITION AND TO PRODUCE CARBON DIOXIDE
                                     11
```

FIG. 1

```
PROVIDING A SOLID COMPOSITION INCLUDING
AT LEAST ONE SHAVING COMPONENT    12
              │
              ▼
ADDING A CARBONATED LIQUID
TO THE SOLID COMPOSITION    13
```

FIG. 2

METHOD AND APPARATUS FOR PRODUCING EFFERVESCENT SHAVING COMPOSITION

This invention relates to shaving compositions.

More particularly, the invention relates to a method and shaving composition which eliminates the need to utilize a pressurized can of foam shaving cream or gel shaving cream and which eliminates the need to utilize in a cup a solid shaving composition which must be admixed with a brush and water to produce shaving cream.

Many shaving compositions are known and can include chemical compositions such as wetting agents, surfactants, foaming agents or lather producing compositions, gelling aids and post-foaming agents, emollients, and/or cleansing agents, and equivalents thereof. A wide variety of such chemical compositions is well known in the art.

Most conventional shaving compositions are dispensed from a pressurized metal can either as a foam or as a gel. After the can is empty, it is discarded.

In addition, a solid shaving composition block in the bottom of a ceramic cup is common and is used by wetting the shaving composition with water and whipping the water and shaving composition on the surface of the block in order to produce a foamy mixture which is applied to a user's face with the brush. After all of the shaving composition in the cup is utilized, the cup is discarded.

While the above-described conventional shaving compositions are widely accepted and are effective, it would be highly desirable to provide an improved shaving composition which did not require the use of a pressurized metal can, ceramic cup, or other similar container to package the shaving composition. It would also be desirable to provide an improved shaving composition which could be carried and transported in a space significantly smaller than that occupied by a conventional pressurized metal can or ceramic cup, and, which would significantly reduce packaging expense by eliminating the need for pressurized cans, ceramic cups, or other bulky containers.

Therefore, it is a principal object of the instant invention to provide an improved shaving composition and method for making the same.

A further object of the invention is to provide an improved shaving composition which need not be packaged in a pressurize can or in a cup.

Another object of the invention is to provide an improved shaving composition which can, in contrast to a pressurized metal can and a ceramic cup, be readily and conveniently carried on the person.

Still a further object of the invention is to provide an improved shaving composition which can be utilized with carbonated water or with regular tap water.

Yet another object of the invention is to provide an improved shaving composition which produces acid when contacted with a fluid.

Yet still a further object of the invention is to provide an improved effervescent shaving composition.

These and other, further and more specific objects and advantages of the invention will be apparent to those skilled in the art from the following detailed description thereof, taken in conjunction with the drawings in which:

BRIEF DESCRIPTION OF THE DRAWINGS

FIG. 1 is a block flow diagram illustrating a method for producing a shaving composition in accordance with the invention;

FIG. 2 is a block flow diagram illustrating an alternate method for producing a shaving composition in accordance with the invention;

Figure 3:
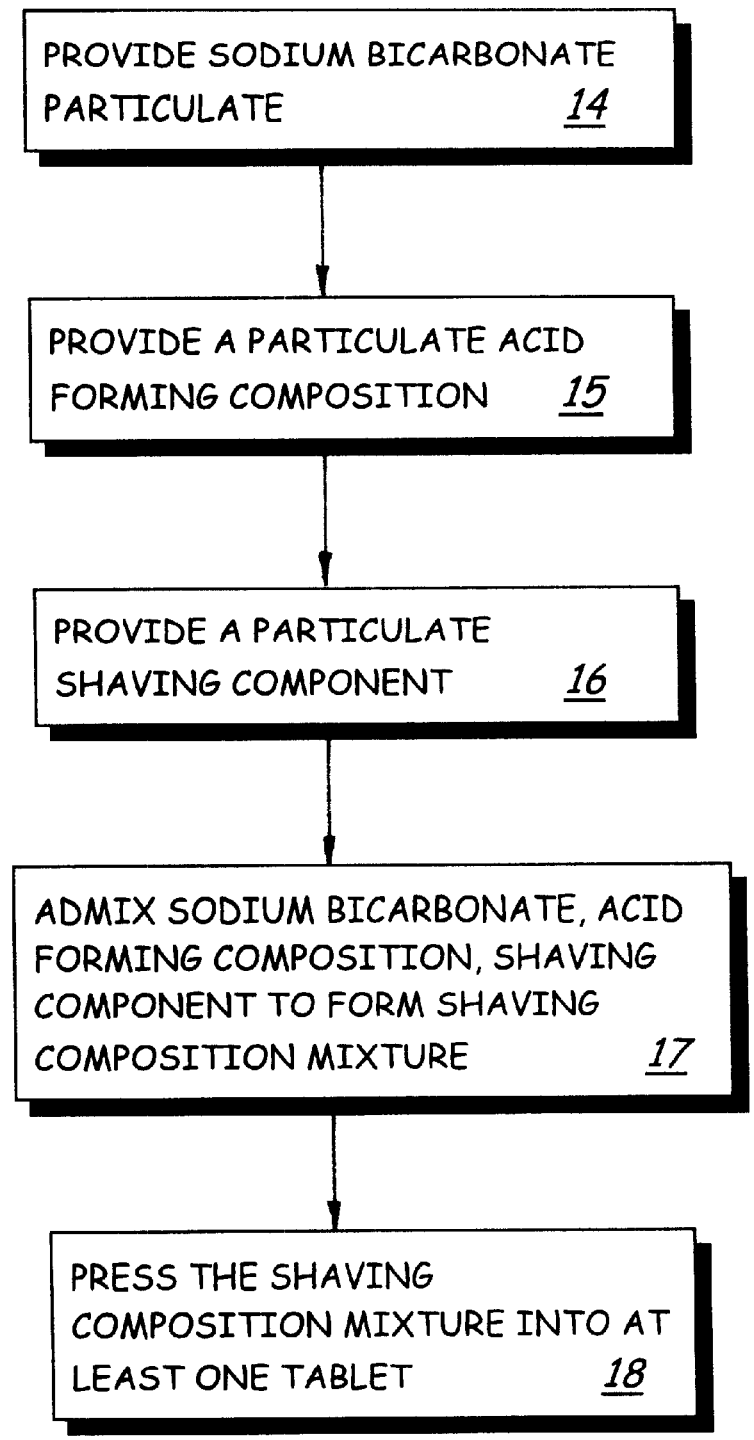
FIG. 3 is a block flow diagram illustrating yet another method for producing a shaving composition in accordance with the invention; and, FIG. 4 is a perspective view illustrating a tablet producing in accordance with the method of FIG. 3.

Briefly, in accordance with my invention, I provide an improved method for producing a shaving composition. The method comprises the steps of providing a solid composition including sodium bicarbonate, an acid-forming composition, and at least one shaving component from a class including a detergent, an emollient, a wetting agent, a binder, and a gelling agent; and, adding a liquid to the solid composition to cause the sodium bicarbonate to react with the acid forming composition to change the pH of the solid composition and to produce carbon dioxide.

In another embodiment of the invention, I provide an improved method for producing a shaving composition. The method comprises the steps of providing a solid particulate composition including a detergent; and, adding a carbonated liquid to the solid composition.

In a further embodiment of the invention, I provide an improved method for producing a shaving composition. The method includes the steps of providing sodium bicarbonate particulate; providing in particulate form an acid forming composition; providing in particulate form at least one shaving component from a class including a detergent, an emollient, a wetting agent, a binder, and a gelling agent; mixing together the sodium bicarbonate particulate, the acid forming composition, and the at least one shaving component to form a shaving composition mixture; and, pressing the shaving composition mixture into at least one tablet. The acid forming composition forms acid when water is added to the tablet. The acid reacts with the sodium bicarbonate to form carbon dioxide.

In another embodiment of the invention, I provide an improved method for shaving. The method includes the steps of providing a solid composition including sodium bicarbonate, an acid-forming composition, and at least one shaving component from a class including a detergent, an emollient, a binder, a wetting agent, and a gelling agent; adding a liquid to the solid composition to cause the sodium bicarbonate to react with the acid forming composition to change the pH of the solid composition and to produce carbon dioxide and cause the composition to effervesce; and, applying the effervescing composition to skin to shave.

Turning now to the drawings, which depict the presently preferred embodiments of the invention for the purpose of illustrating the practice thereof and not by way of limitation of the scope of the invention, FIG. 1 illustrates a method for producing a shaving composition including the step 10 of "provide solid composition including sodium bicarbonate, an acid forming composition, and at least one shaving component; and, step 11 of "add liquid to the solid composition to cause the sodium bicarbonate to react with the acid forming composition to change the pH of the solid composition and produce carbon dioxide.

The liquid added to the solid composition is presently preferably water, but can comprise alcohol or any other desired liquid.

The acid forming composition can, by way of example and not limitation, comprise citric acid, comprise cream of tartar and tartaric acid, comprise a phosphate power including calcium dihydrogen phosphate comprise a sulfate powder including sodium aluminum sulfate (alum). Sulfate powder does not react until heated and is the slowest acting acid forming composition. Tartrate and phosphate powders are the fastest. They react as soon as they are mixed with a liquid. The acid forming composition is normally utilized in a particulate or powder form to produce a shaving composition in accordance with the invention.

The shaving component can include one or more components selected from the class consisting of detergents, emollients, wetting agents, and gelling agents.

There are many known detergents which can be applied to a person's skin. Some examples, without limitation, are sodium lauryl sulfate, ammonium lauryl sulfate, triethanolamine lauryl sulfate, and magnesium lauryl sulfate. Such detergents ordinarily must be in dry powder form to be utilized in the practice of the invention.

Examples of emollients which can, without limitation, be utilized in the practice of the invention include glycerin and sodium PCA.

An example of a gelling agent is carrageenan. Many such thickeners or gelling agents are well known in the art.

The shaving composition can also include starch or another component which functions either as a binder or to keep the shaving composition dry until a liquid is added to the composition. Any desired binding agent can be utilized.

Once the shaving composition of FIG. 1 is produced, it can be pressed into a tablet or remain in powder form. When in powder form, the shaving composition can, if desired, be packaged in a capsule, in a small paper pack, etc. In use, the shaving composition of FIG. 1 is utilized by adding water or another liquid. The liquid causes the acid forming composition to interact with the sodium bicarbonate to form a foamy shaving composition which is applied to the skin prior to shaving. Since a relatively thick, foamy composition is typically desired, only minimal amounts of water are added to the shaving composition, although the amount of water utilized can vary as desired.

FIG. 2 illustrates an alternate method for producing a shaving composition including the step 12 "providing a solid composition including at least one shaving component"; and, step 13 "adding a carbonated liquid to the solid composition". In the method of FIG. 2, it is not necessary to include sodium bicarbonate and an acid forming composition do not have to be included in the solid composition because the carbonation already exists in liquid—for example seltzer water or a soft drink—being added to the solid composition. If desired, however, sodium bicarbonate and an acid forming composition can be including in the solid composition of step 12 even though a carbonated liquid is utilized. Although the quantity of carbonated liquid can vary as desired, ordinarily only the quantity necessary to produce a lather is added to the solid composition. After the carbonated liquid is added, the resulting lather is applied to the skin prior to shaving.

Figure 4:
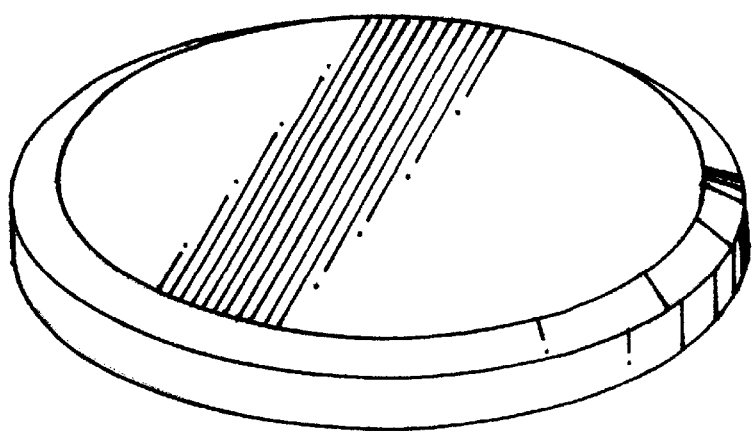

The alternate method of the invention illustrated in FIG. 3 includes step 14 "provide sodium bicarbonate particulate"; step 15 "provide a particulate acid forming composition"; step 16 "provide a particulate shaving component"; step 17 "admix the sodium bicarbonate particulate, the particulate acid forming composition, and the particulate shaving component to form a shaving composition mixture"; and, step 18 "press the shaving composition mixture into at least one tablet". One possible resulting tablet is illustrated in FIG. 4. In use of the tablet of FIG. 4, water or another liquid is added to the tablet to soften the tablet into a lather and to produce a foaming action by causing the sodium bicarbonate to interact with the acid forming composition to produce carbon dioxide. The resulting lather is applied to the skin prior to shaving.

One principal advantage of the invention is that each shaving tablet or portion of powder necessary to shave once occupies a small amount of space and can be readily carried on the person or in a travel bag. It is also a simple matter for a hotel to provide such a tablet or portion of powder to enable a person staying overnight in the hotel to shave without having a carry the conventional pressurized metal can filled with shaving cream.

The following are provided by way of example, and not limitation.

EXAMPLE 1

The following are provided in powder form.

| Component | Grams |
| --- | --- |
| Sodium Bicarbonate | 31.0 |
| Sodium Lauryl Sulfate, 100% Active | 63.0 |
| Citric Acid | 1.0 |
| TOTAL | 95.0 |

The sodium bicarbonate is admixed with the sodium lauryl sulfate, after which the citric acid is admixed to form a solid composition comprised of powder. A shaving composition results. Water is added to the composition to produce carbon dioxide and form a lather.

EXAMPLE 2

Example 1 is repeated, except two grams of liquid glycerin is included as an emollient and binder. The powder is pressed into tablet form. When the tablet is utilized for shaving, the tablet is contacted with a small amount of water to produce carbon dioxide and form a lather. If too much water is added the lather is not as thick as desired.

EXAMPLE 3

The following are provided in powder form, except for the sodium PCA, which is in a liquid form.

| Component | Grams |
| --- | --- |
| Sodium Bicarbonate | 31.0 |
| Magnesium Lauryl Sulfate | 62.0 |
| Phosphate Powder | 2.0 |
| Calcium dihydrogen acid | |
| Sodium PCA | 5.0 |
| TOTAL | 100.0 |

The sodium bicarbonate is admixed with the magnesium lauryl sulfate, after which the phosphate powder is admixed to form a solid composition comprised of powder. The sodium PCA is then admixed. A shaving composition results. Alcohol is added to the composition to produce a lather and carbon dioxide.

The amount of carbon dioxide produced in the methods of the invention can vary as desired. If large amounts of carbon dioxide are desired, larger amounts of sodium bicarbonate and the acid forming composition are utilized. If small amounts of carbon dioxide are desired, smaller amounts of sodium bicarbonate and the acid forming composition are utilized.

EXAMPLE 4

The shaving composition of Example 1 is provided. A small amount of water sufficient to produce a thick effervescing lather is produced. The lather is applied to the user's skin while effervescing. The effervescing appears to facilitate the interaction of the lather with the user's skin and to improve the cleaning of the skin by the detergent in the lather. The carbon dioxide bubbles also appear to produce a comfortable relaxing sensation in the skin.

Having described my invention in such terms as to enable those skilled in the art to make and use the invention, and having described the presently preferred embodiments thereof, I claim:

1. A method of shaving, comprising the steps of
   (a) providing a quantity of sodium bicarbonate having a selected weight;
   (b) providing a quantity of an acid forming composition having a selected weight;
   (c) providing a quantity of a detergent having a selected weight, said selected weight of said detergent being greater than the combined weight of said sodium bicarbonate and said acid forming composition;
   (d) admixing said sodium bicarbonate, said acid forming composition, and said detergent to producing a shaving composition;
   (e) adding water to said shaving composition to cause said sodium bicarbonate to react with said acid forming composition and cause said composition to effervesce and produce a lather;
   (f) applying said lather to an area of skin; and,
   (g) shaving said area of skin.

2. A method of shaving, comprising the steps of
   (a) providing a quantity of sodium bicarbonate having a selected weight;
   (b) providing a quantity of an acid forming composition having a selected weight;
   (c) providing a quantity of a detergent having a selected weight, said selected weight of said detergent being greater than the combined weight of said sodium bicarbonate and said acid forming composition;
   (d) admixing said sodium bicarbonate, said acid forming composition, and said detergent to produce a shaving composition;
   (e) adding water to said shaving composition to cause said sodium bicarbonate to react with said acid forming composition, cause said composition to effervesce;
   (f) applying said effervescing composition to an area of skin;
   (g) shaving said area of skin.

3. A method of shaving, comprising the steps of
   (a) providing a quantity of a detergent;
   (b) adding a quantity of a carbonated liquid to the detergent to produce a lather;
   (c) applying said lather to an area of skin;
   (d) shaving said area of skin.

* * * * *